United States Patent
Wood et al.

(10) Patent No.: US 7,229,258 B2
(45) Date of Patent: *Jun. 12, 2007

(54) STREAMLINED UNOBSTRUCTED ONE-PASS AXIAL-FLOW PUMP

(75) Inventors: Houston G. Wood, Salt Lake City, UT (US); Paul E. Allaire, Charlottesville, VA (US); Don B. Olsen, Salt Lake City, UT (US); Steven W. Day, Davis, CA (US); Xinwei Song, Richmond, VA (US); Alex Untaroiu, Charlottesville, VA (US); Amy Throckmorton, Charlottesville, VA (US)

(73) Assignees: Medforte Research Foundation, Salt Lake City, UT (US); University of Virginia Patent Foundation, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/950,176

(22) Filed: Sep. 24, 2004

(65) Prior Publication Data
US 2005/0135942 A1    Jun. 23, 2005

Related U.S. Application Data

(60) Provisional application No. 60/506,023, filed on Sep. 25, 2003.

(51) Int. Cl.
*F04B 35/04* (2006.01)
*A61M 1/10* (2006.01)

(52) U.S. Cl. .............. 417/355; 417/365; 417/423.15; 623/3.13; 623/3.14

(58) Field of Classification Search ................ 417/352, 417/353, 423.15, 365, 356, 355; 623/3.14, 623/3.13
See application file for complete search history.

(56) References Cited

U.S. PATENT DOCUMENTS

| | | | |
|---|---|---|---|
| 3,864,055 | A | 2/1975 | Kletschka et al. |
| 3,890,019 | A | 6/1975 | Boden et al. |
| 4,121,143 | A | 10/1978 | Habermann et al. |
| 4,166,466 | A | 9/1979 | Jarivk |
| 4,180,946 | A | 1/1980 | Heijkenskjold et al. |
| 4,302,854 | A | 12/1981 | Runge |
| 4,382,199 | A | 5/1983 | Isaacson |

(Continued)

OTHER PUBLICATIONS

Kannel WB, www.ncbi.nlm.nih.gov/entrez/query.fcgi?cmd=Retrieve&db=pubmed &dopt=abstract..., "Epidemiological Aspects of Heart Failure" Sep. 16, 2004.

(Continued)

*Primary Examiner*—Charles G. Freay
(74) *Attorney, Agent, or Firm*—Thorpe North & Western

(57) ABSTRACT

A blood pump has an impeller rotatably disposed and magnetically suspended within a cavity of a stator by a plurality of magnetic bearings (passive permanent and active electromagnetic) having impeller magnets on the impeller and stator magnets or coils/poles on the stator. A motor includes impeller magnets on the impeller and coils/poles associated with the stator. A single, annular blood flow path extends axially through the cavity between the impeller and the stator, and between the impeller magnets on the impeller and the stator magnets or the coils/poles on the stator.

21 Claims, 7 Drawing Sheets

U.S. PATENT DOCUMENTS

| | | |
|---|---|---|
| 4,392,693 A | 7/1983 | Habermann et al. |
| 4,625,712 A | 12/1986 | Wampler |
| 4,662,358 A | 5/1987 | Farrar |
| 4,688,998 A | 8/1987 | Olsen et al. |
| 4,763,032 A | 8/1988 | Bramm et al. |
| 4,779,614 A | 10/1988 | Moise |
| 4,781,525 A | 11/1988 | Hubbard et al. |
| 4,817,586 A | 4/1989 | Wampler |
| 4,906,229 A | 3/1990 | Wapler |
| 4,908,012 A | 3/1990 | Moise et al. |
| 4,944,748 A | 7/1990 | Bramm et al. |
| 4,994,078 A | 2/1991 | Jarvik |
| 5,040,944 A | 8/1991 | Cook |
| 5,049,134 A | 9/1991 | Golding |
| 5,055,005 A | 10/1991 | Kletschka |
| 5,078,741 A | 1/1992 | Bramm et al. |
| 5,112,202 A | 5/1992 | Oshima et al. |
| 5,195,877 A | 3/1993 | Kletschka |
| 5,321,342 A | 6/1994 | Kruse |
| 5,326,344 A | 7/1994 | Bramm et al. |
| 5,360,317 A | 11/1994 | Clausen |
| 5,370,509 A | 12/1994 | Golding |
| 5,385,581 A | 1/1995 | Bramm et al. |
| 5,470,208 A | 11/1995 | Kletschka |
| 5,507,629 A | 4/1996 | Jarvik |
| 5,527,159 A | 6/1996 | Bozeman |
| 5,603,337 A | 2/1997 | Jarvik |
| 5,613,935 A | 3/1997 | Jarvik |
| 5,695,471 A | 12/1997 | Wampler |
| 5,725,357 A | 3/1998 | Nakazeki et al. |
| 5,911,558 A | 6/1999 | Nakazeki et al. |
| 5,928,131 A * | 7/1999 | Prem .................... 600/16 |
| 5,947,892 A | 9/1999 | Benkowski |
| 6,015,272 A | 1/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,120,537 A | 9/2000 | Wampler |
| 6,155,969 A | 12/2000 | Schima et al. |
| 6,201,329 B1 | 3/2001 | Chen |
| 6,227,820 B1 | 5/2001 | Jarvik |
| 6,234,772 B1 | 5/2001 | Wampler et al. |
| 6,244,835 B1 * | 6/2001 | Antaki et al. ........... 417/356 |
| 6,293,901 B1 | 9/2001 | Prem |
| 6,302,661 B1 | 10/2001 | Khanwilkar et al. |
| 6,368,075 B1 | 4/2002 | Fremerey |
| 6,368,083 B1 | 4/2002 | Wampler |
| 6,375,607 B1 | 4/2002 | Prem |
| 6,394,769 B1 | 5/2002 | Bearnson et al. |
| 6,447,266 B2 | 9/2002 | Antaki et al. |
| 6,527,521 B2 | 3/2003 | Noda |
| 6,527,699 B1 | 3/2003 | Goldowsky |
| 6,595,762 B2 | 7/2003 | Khanwilkar et al. |
| 6,609,883 B2 | 8/2003 | Woodard et al. |
| 6,623,475 B1 | 9/2003 | Siess |
| 6,638,011 B2 | 10/2003 | Woodard et al. |
| 6,638,083 B2 | 10/2003 | Wampler |
| 6,688,861 B2 | 2/2004 | Wampler |
| 6,716,157 B2 | 4/2004 | Goldowsky |
| 6,717,311 B2 | 4/2004 | Locke |
| 6,761,532 B2 * | 7/2004 | Capone et al. ........... 415/200 |

OTHER PUBLICATIONS

*The Artificial Heart, Executive Summary and The Artificial Heart Program*: Current Status and History pp. 1-25.

Song, Xinwei, Throckmorton, Amy L., Untaroiu, Alexandrina, Patel, Sonna, Allaire, Paul E., Wood, Houston G., and Olsen, Don B. "*Axial Flow Blood Pumps*" ASAIO Journal 2003; 49: pp. 355-364.

Olsen, Don B. "The History of Continuous-Flow Blood Pumps" Presidential Address, Utha Artificial Heart Research Institute, Salt Lake City, Utah Mar. 2000, 401-404, Presented in part at the 7th congress of the International society for Rotary Blood Pumps held Aug. 26-27, 1999 in Tokyo, Japan.

Kim, Hee Chand, Bearnson, Gill B., Khanwilkar, Pratap S., Olsen, Don B., Maslen, Eric H. , Allaire, Paul E. "*In Vitro Characterization of a Magnetically Suspended Continuous Flow Ventricular Assist Device*", Department of Biomedical Engineering, Seoul Korea, pp. M359-M364.

Hilton, Edgar F , Allaire, Paul E., Wei, Naihong, Baloh, Michael J., Bearnson, Gill, Olsen, Don B., and Khanwilkar, Pratap "Test Controller Design, Implementation, and Performance for a Magnetic Suspension Continuous Flow Ventricular Assist Device" Dec. 1998; revised Feb. 1999, Presented in part at the 6th Congress of the International Society for Rotary Blood Pumps, Jul. 25-27, 1998, Park City, Utah, Artificial Organs, vol. 23, No. 8, 1999 pp. 785-791, Blackwell Science Inc.

Bearnson, B., Maslen, Eric H., Olsen, Don B., Allaire, Paul E., Khanwilkar, Pratap S., Long, James W., and Kim, Hee Chan "*Development of a Prototype Magnetically Suspended Rotor Ventricular Assist Device*", ASAIO Journal 1996; 42: pp. 275-281.

Allaire, P.E., Kim, H.C., Maslen, E.H., Olsen, D.B., and Bearnson G.B. "*Prototype Continuous Flow Ventricular Assist Device Supported on Magnetic Bearings*" Artificial Organs, 20(6):582-590, Blackwell Science, Inc, Boston 1996 International Society for Artificial Organs.

Anderson, Jay B., Wood, Houston G., Allaire, Paul E., McDaniel, James C., Olsen, Don B., Bearnson, G., "*Numerical Studies of Blood Shear and Washing in a Continuous Flow Ventricular Assist Device*": ASAIO Journal 2000; 46: pp. 486-494.

Day, Steven W. , McDaniel, James C., Wood, Houston G., Allaire, Paul E., Lnadrot, Nicolas and Curtas, Anthony "*Particle Image Velocimetry Measurements of Blood Veloctiy in a Continuous Flow Ventricular Assist Device*" ASAIO Journal 2001; 47:406-411.

O'Connell, John B., Bristow, Michael R., "*Economic Impact of Heart Failure in the United States; Time for a Different Approach*": The Journal of Heart and Lung Translpantation Jul./Aug. 1993 pp. S107-S112.

Blackshear, Perry L. "*Mechanical Engineering Aspects of Rotary Blood Pumps*": International Workshop on Rotary Blood Pumps Baden, Austria Sep. 9-11, 1991.

\* cited by examiner

STREAMLINED UNOBSTRUCTED ONE-PASS AXIAL-FLOW PUMP

PRIORITY CLAIM

Benefit is claimed of U.S. Provisional Patent Application Ser. No. 60/506,023 filed on Sep. 25, 2003, which is herein incorporated by reference.

This application is related to U.S. patent application Ser. No. 10/949,884, filed Sep. 24, 2004, which is herein incorporated by reference.

GOVERNMENT RIGHTS

The U.S. Government has a paid-up license in this invention and the right in limited circumstances to require that the patent owner to license others on reasonable terms as provided for by the terms of Grant No. NIH HL64378 awarded by the National Institutes of Health (NIH).

BACKGROUND

1. Field of the Invention

The present invention relates generally to axial-flow blood pumps suitable for permanent implantation in humans as a chronic ventricular assist device.

2. Related Art

An effective and reliable axial-flow blood pump can provide mechanical circulatory support (MCS) to thousands of patients each year. An estimated 4.8 million Americans suffer from congestive heart failure (CHF), a clinical syndrome that involves ventricular dysfunction and ultimately a reduction in cardiac output. A reduction in cardiac output leads to poor perfusion, fluid accumulation, and activation of salt-water retention mechanisms. Statistics from the American Heart Association indicate that approximately 400,000 new CHF cases are diagnosed each year in the United States, and an estimated 40,000 cardiac failure patients die each year due to CHF.

If short-term medical intervention, whether surgical or through aggressive medications, is not successful, then many of these heart failure patients become candidates for cardiac transplantation. Due to a limited number of donor hearts available each year (~2,500), CHF patients often require MCS as a bridge-to-transplantation and many such patients may fail to survive awaiting a donor organ. Ventricular assist devices (VADs) or mechanical blood pumps have proven successful in bridge-to-cardiac transplant support of patients suffering from end-stage heart failure and encourage the belief that long-term MCS or destination therapy is possible. An estimated 35,000 to 70,000 cardiac failure patients could benefit from long-term MCS each year.

Despite the tremendous need for an effective ventricular assist pump, prior MCS devices have not been entirely successful due to several limiting factors. Particular concerns and design limitations of current blood pump designs include: 1) component durability and lifetime; 2) blood clotting or thrombosis due to flow stasis within the pump in secondary flow areas, wash ports, and recirculation regions, and platelet activation in regions of high shear stress; 3) blood trauma or hemolysis that may occur when blood contacts mechanical bearings or foreign surfaces, and when blood is subjected to higher than normal shear conditions due to rotating components; 4) percutaneous leads which are needed for the motor and bearing control systems and other support lines; 5) pump geometry (size, shape, and weight) for ease of implantation, patient mobility, avoidance of graft tears; 6) high cost of the pump; and 7) high power demand that requires a large power supply.

Many early blood pump designs were constructed in a pulsatile configuration. These required the explantation (removal) of the diseased native heart and the replacement by the pulsatile mechanical blood pump. These pulsatile pumps, however, have proven to be very complicated mechanically, are relatively large and have relatively short mechanical lifetimes. An alternative design using a rotary pump leads to the use of the mechanical heart as a ventricular assist device which does not require explantation of the native heart. The rotary pumps have smaller size and better mechanical reliability. Such a pump aids a patient's heart by pumping additional blood in parallel with a diseased heart. The rotary blood pump may be connected to the patient's heart in a left-ventricular assist configuration, a right-ventricular assist configuration, or a biventricular assist configuration. For instance, if the left-ventricular configuration is adopted, the rotary pump is connected to receive flow from the left ventricle of the heart and return it to the aorta. Generally the rotary pump includes a stator (housing) having an inlet and outlet port, an impeller positioned within the stator and having impeller blades to create the pumped blood flow, a motor for rotating the pump and a suspension system. The blood enters the inlet of the stator and is pumped by the rotating impeller through the housing to the outlet, and back into the patient's circulatory system.

There are two primary configurations that are used for rotary blood pump configurations: axial flow and centrifugal flow. In the axial flow configuration, the pump configuration is similar to a cylinder with inlet flow port at one end and exit flow port at the other end. The centrifugal flow configuration is similar to a circular disk with an inlet flow port at the center of one side of the disk, oriented perpendicular to the plane of the disk, and a tangential exit flow port at the periphery of the disk, in the plane of the disk.

Studies have shown several problems with poor rotary blood flow path design in both axial flow and centrifugal flow blood pumps including those with magnetic suspension. One of these problems is stagnation resulting in thrombosis or clotting. If the flow undergoes a low or zero velocity region, it may experience thrombosis or clotting, where blood resides on the pump structure. Such low or zero velocity regions are usually found in secondary blood paths in the pump. As the thrombosis builds up, a section or large clot may break off and embolize in the blood stream. If the clot occludes a blood vessel that enters the brain or other sensitive area, very serious conditions may develop, such as profound organ dysfunction, such as seizure or severe brain damage. Another problem is hemolysis, where blood is exposed to high shear stresses in the rotary pump, usually near the impeller blades which move at relatively high speed, and which may cause direct or delayed damage to the circulating blood. As the impeller applies forces to the blood, regions of turbulence and/or jet formation, can occur in poorly designed devices.

Many rotary blood pump designs have been created to overcome these bearing problems with their use as ventricular assist devices. It is desired to have a bearing system with an expected operating lifetime of 10 to 20 years, if possible. Generally, these bearings fall into three categories: mechanical, hydrodynamic or magnetic bearings.

Some rotary blood pumps have mechanical or hydrodynamic bearings or hydrodynamic suspensions. For example, see U.S. Pat. Nos. 6,609,883 and 6,638,011. Other rotary blood pumps have a combination of hydrodynamic bearings and permanent magnet bearings. For example, see U.S. Pat. Nos. 5,695,471; 6,234,772; 6,638,083 and 6,688,861.

One type of rotary blood pump has mechanical bearings which require a lubricant flush or purge with an external lubricant reservoir for lubricating the bearings and carrying away heat. For example, see U.S. Pat. Nos. 4,944,722 and 4,846,152. There are many disadvantages to this type of pump. The percutaneous supply and delivery of the lubricant purge fluid degrades the patient's quality of life and provides a high potential for infection. Seals for the external lubricant are notoriously susceptible to wear and to fluid attack which may result in leakage and the patient having a subsequent seizure. Also, an additional pump is needed for delivery of the lubricant to the bearing, and if it fails the lubricated bearing freezes. Finally, the mechanical bearings have a finite wear life, usually of a few years, and need to be replaced due to the bearing wear.

There are axial flow rotary pumps with ceramic bearings presently under clinical trials. It is not known how long these bearings might last but expected lifetimes based upon other applications are in the range of 2 to 5 years. Also, there have been reported cases of thromboembolism in some patients. This has occurred while the patients are being anticoagulated.

Rotary pumps have been developed with magnetic suspension to overcome the earlier need for an external purge of lubricant or ceramic mechanical bearings. Utilizing a magnetically suspended impeller eliminates direct contact between the rotary and stationary surfaces, such as found in mechanical bearings. For example, see U.S. Pat. Nos. 5,326,344 and 4,688,998. Expected operating lifetimes of magnetic suspension systems range from 10 to 20 years. This type of rotary pump with magnetic suspension generally includes an impeller positioned within a housing, with the impeller supported and stabilized within the housing by a combination of permanent magnets positioned in the impeller and the stator, and with an electromagnet positioned within the stator. The impeller is rotated by a ferromagnetic motor consisting of a stator ring mounted within the housing, and electromagnetic coils wound around two diametrically opposed projections. The ferromagnetic impeller and the electromagnetic coils are symmetrically positioned with respect to the rotary axis of the pump impeller.

In magnetically suspended rotary blood pumps the gap between the stator and the impeller serves the competing purposes of allowing the blood to pass through, as well as assisting with the magnetic suspension and rotation of the impeller. For the blood flow, the radial gap is desired to be large for efficient blood pumping, but for efficient magnetic suspension, the radial gap is desired to be small. Because of the competing gap requirements, other prior art pumps often include a primary fluid flow region and a secondary magnetic gap. The primary fluid flow radial gap region is large enough to provide for hydrodynamically efficient flow without traumatic or turbulent fluid flow. The secondary magnetic radial gap allows for fluid therethrough which is small enough to provide for efficient magnetic levitation of the central hub, which can be either the stator or the impeller. Examples of pumps with a blood flow path including both a primary and secondary blood path can be found in U.S. Pat. Nos. 6,071,093; 6,015,272; 6,244,835 and 6,447,266.

Some prior art blood pumps include a permanent magnet thrust bearing which has a relatively large diameter thrust disk with permanent magnets having an alternating polarity configuration on both the stator and rotor components of the pump, but oriented in a radial configuration. It is believed that the large thrust disk obstructs the blood path and creates a tortuous blood path which is far from straight through the pump. The prior art pumps, however, include radially polarized permanent magnet configurations.

Various sensing techniques have been used to locate and control the rotor position of an active electromagnetic bearing. These techniques include eddy current or inductive, capacitive, and laser sensors, commonly used in industrial applications of electromagnetic bearings. Laser sensors cannot be used because they cannot "look through" the opaque blood. Eddy current and inductive sensors require a magnetic source in the stator and a magnetic target in the rotor as well as a magnetic path running between the stator and rotor used to sense the rotor position. Capacitance probes require an electrical path between the stator and rotor which is generally not feasible with blood pumps.

There are several problems associated with the use of an eddy current or inductive sensor types in the gap in between the stator and rotor of an implantable miniature blood pump. For example, these types of sensors rely on a clear magnetically un-obstructed pathway between the sensor "face" and the rotor surface. This means that the sensor body must be placed within the stator housing with its "face" perpendicular to the rotor surface. It is desired to avoid having any part of the body of the sensor placed within the fluid stream (blood) of the pump, yet placed it close to the rotor magnetic target. One problem with these types of sensors is the possible contamination of the blood stream if the soft iron or other non-biocompatible sensor faces are exposed to the blood. Generally this is solved with the use of some sort of thin biocompatible material covering the sensor face and target to avoid blood contact. Other problems are space constraints required for the sensor, and the energy budget required for such sensors.

In addition, such rotary blood pumps include a motor to rotate the impeller which, in turn, produces the needed blood flow. It is desirable that the motor have very long operating life, and operate fault free during a range of time up to one or more decades of service. Some pumps use brashness DC motors for this purpose which have a compact and efficient design without brushes. There is no brush wear so the expected life of such pumps is very long. One issue with such pumps is assuring that the motor will start in the necessary direction for the impeller to pump. The proper start up direction of rotation can be an important issue.

As noted above, magnetic suspensions often include at least one active control electromagnetic bearing axis. In a radial bearing configuration, the electromagnet can consist of a set of soft iron magnetic poles in a configuration in the stator arrayed circumferentially around the rotor with a clearance gap and imposing centering forces acting upon a soft iron placed in the rotor. The current in the coils must be controlled properly to achieve the desired centering purpose, allowing the rotor to properly operate in the clearance space. The current in the coils are adjusted by an automatic control system. In order to carry out the automatic force centering control method, there must be a sensor to sense the position or displacement of the rotor magnetic target, an electronic means of active control to adjust the control currents in the stator coils, such as electronic controller boards and power amplifiers to provide the power.

The control methods for determining the coil currents in the magnetic bearing of an active bearing can involve a manner of specifying how the coil currents are to be obtained. Active magnetic bearings can be composed of soft iron magnetic materials which have a significant limitation in that they are subject to magnetic saturation at a certain level, typically at about 1 Tesla. The active control method should take that fact into account. Also, the force exerted by an active magnetic bearing is a nonlinear function of both the magnetic gap and the current in the coils.

The most common method of dealing with both the magnetic material saturation and the nonlinearity is that of bias linearization, where a steady state bias current is imposed on each of the coil currents, which produces a magnetic flux in the soft magnetic iron poles of approximately one half of the magnetic saturation flux. Then a perturbation current is applied to produce changes in the coil currents associated with the poles on one side of the rotor relative to the other side. In turn, when these differences due to higher coil currents associated with the poles on one side produce higher magnetic forces on the rotor magnetic target compared to the other side, where lower coil currents associated with poles on the other side of the rotor produce lower magnetic forces acting on the rotor magnetic target. The rotor has a net force which is employed to center it in the clearance gap. The use of the bias linearization method, as just described, has a major disadvantage that it has relatively high power consumption in the coils, and generates large heating in the coils which may overheat the active magnetic bearing component of the rotary blood pump. Further, there are limitations on this type of bias linearization which prevent the full utilization of the magnetic force capacity of the active magnetic bearing.

Another issue with regard to proper centered operation of the rotary pump impeller is the unbalance in the rotor. Rotating devices are subject to mechanical unbalance as it is difficult to manufacture a perfectly balanced rotor. In addition, during operation within the patient over a long period of time, additional changes in unbalance may take place due to rotor component shifting, rotor rubbing, blood or blood products adhesion to the impeller surfaces, and other factors.

As the patient undergoes different levels of activity, the non-centering forces acting upon the rotor change. When the patient is active, such as in walking or climbing stairs, the magnetic current biasing levels in the active magnetic bearing are required to be high to provide high magnetic centering forces. However, when the patient is sitting quietly or sleeping, much less magnetic bearing centering force is needed. Higher bias current levels result in higher power consumption and higher heating.

In addition, centrifugal flow rotary blood pumps with magnetic suspension have been proposed. For example, see U.S. Pat. Nos. 6,074,180; 6,595,762, and 6,394,769. It has been found, however, that centrifugal flow pumps are not easily implantable in either animals or humans because the inflow and outflow cannulas are located at 90 degrees relative to each other and in separate planes. In addition, such centrifugal pumps require convoluted secondary blood flow paths as part of the design.

SUMMARY OF THE INVENTION

It has been recognized that it would be advantageous to develop a reliable ventricular assist device for permanent implantation in humans. In addition, it has been recognized that it would be advantageous to develop a blood pump to reduce coagulation, avoid secondary flow paths, and provide an open, one-pass blood path. In addition, it has been recognized that it would be advantageous to develop a blood pump with a reduced size, long operational life and lower power consumption requirements. In addition, it has been recognized that it would be advantageous to develop a blood pump with a hybrid permanent magnet and electromagnetic set with permanent magnets to manage greater forces (axial or thrust) and an electromagnet to manage lesser forces (radial). In addition, it has been recognized that it would be advantageous to develop a blood pump with optimum configuration permanent and electromagnetic bearings to enable the best blood pump flow performance. In addition, it has been recognized that it would be advantageous to develop a blood pump with proper start up direction of rotation. In addition, it has been recognized that it would be advantageous to develop a blood pump with control methods that consume less power and produce less heat to facilitate an active magnetic bearing component.

The invention provides a blood pump with an impeller rotatably disposed and magnetically suspended within a cavity of a stator by a plurality of magnetic bearings (passive permanent and active electromagnetic) having impeller magnets on the impeller and stator magnets or coils/poles on the stator. A motor includes impeller magnets on the impeller and coils/poles associated with the stator. A single, annular blood flow path extends axially through the cavity between the impeller and the stator, and between the impeller magnets on the impeller and the stator magnets or the coils/poles on the stator.

Additional features and advantages of the invention will be apparent from the detailed description which follows, taken in conjunction with the accompanying drawings, which together illustrate, by way of example, features of the invention.

Figure 1:
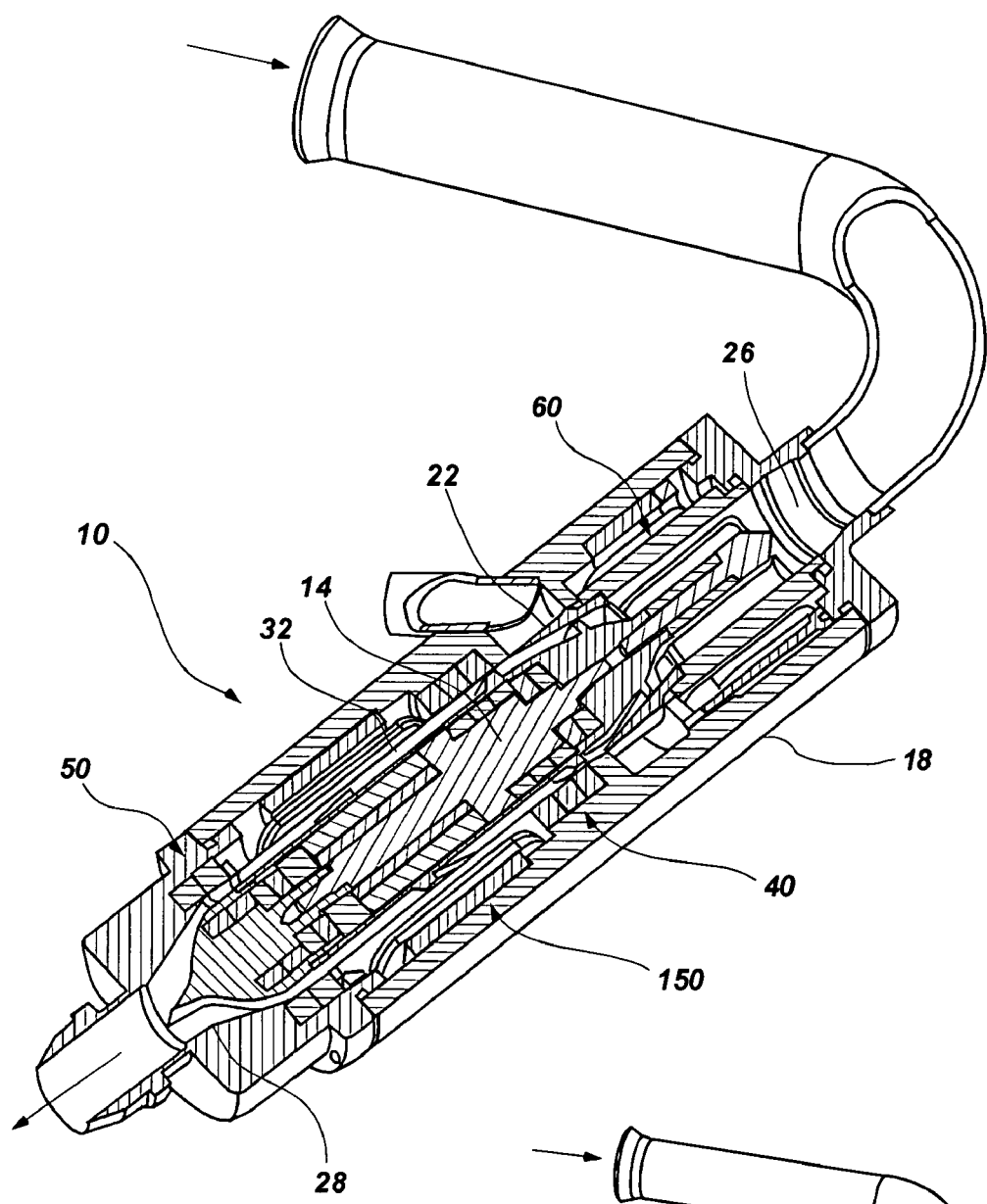
FIG. 1 is a longitudinal cross-sectional perspective view of a blood pump in accordance with an embodiment of the present invention.
Figure 2:
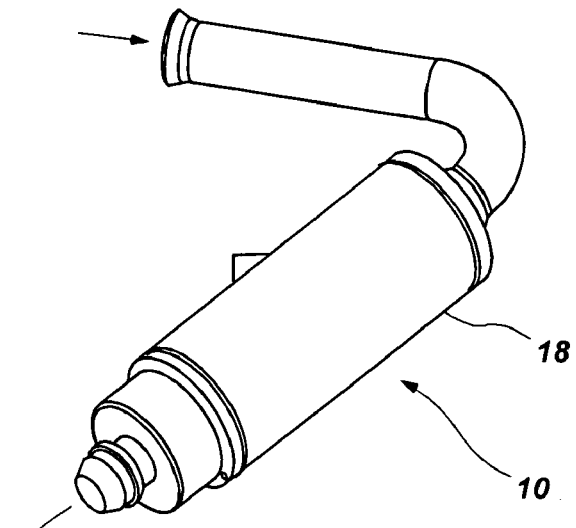
FIG. 2 is perspective view of the blood pump of FIG. 1.

Reference will now be made to the exemplary embodiments illustrated in the drawings, and specific language will be used herein to describe the same. It will nevertheless be understood that no limitation of the scope of the invention is thereby intended.

DETAILED DESCRIPTION OF PREFERRED AND ALTERNATIVE EXAMPLE EMBODIMENTS

As illustrated in FIGS. 1–8 and 10a–14b, an exemplary embodiment of a compact, axial flow, rotary blood pump, indicated generally at 10, is shown with a magnetic suspension and rotating system. Such a pump can be utilized as a ventricular assist device (VAD) for those who suffer from congestive heart failure (CHF). The pump 10 advantageously includes a magnetic suspension and rotating system that reduces size, has long operational life and lowers power consumption requirements. In addition, the pump 10 advantageously includes an unobstructed one-pass blood design without a secondary blood path for any magnetic suspension clearances, as opposed to previous magnetic suspension systems requiring both primary and secondary blood paths. Thus, the pump 10 advantageously minimizes the incidence of flow stasis leading to thrombosis, as well as hemolysis by avoiding secondary flow paths The magnetic suspension uses 1) one permanent magnet, passive, axially centering, thrust bearing; 2) one permanent magnet passive, radially centering bearing and 3) one active, electromagnetic, radial bearing, as described in greater detail below. Thus, the power consumption is minimized because only one active electromagnetic bearing is employed that consumes power, and the other bearings are permanent bearings that consume no power. In addition, the permanent bearings do not heat the pump, nor do they require wires, or any power supply or electronic controllers. Furthermore, this magnetic suspension configuration contributes to the single pass blood path, without requiring any secondary blood path, which also minimizes the power consumption, wire count, power supplies, and electronic controllers.

The pump 10 includes a pump rotor or impeller 14 magnetically suspended in an axial flow pump stator or housing 18. The stator 18 includes a cavity 22 extending axially therethrough between an inlet 26 and an outlet 28. The cavity 22 of the stator 18 can have a continuous and sealed liner 29 or can, separating stator components from the impeller and fluid passage, as described in greater detail below. The impeller 14 is rotatably disposed in, and magnetically suspended in, the cavity 22 or liner 29. The impeller 14 defines an axis of rotation 30 about which the impeller rotates. In addition, a gap or a fluid passage 32 is defined between the impeller 14 and the stator 18 through which the blood flows. Thus, the blood enters through the inlet 26, flows around the impeller 14, through the fluid passage 32, and out of the outlet 28, forming the single pass blood path. The cavity 22 and the stator 18 can also extend along the axis of rotation 30. In addition, the inlet 26 and outlet 28 can be aligned longitudinally or axially. The cavity 22 and impeller 14 can have elongated, substantially cylindrical shapes that taper at the ends.

Figure 5:
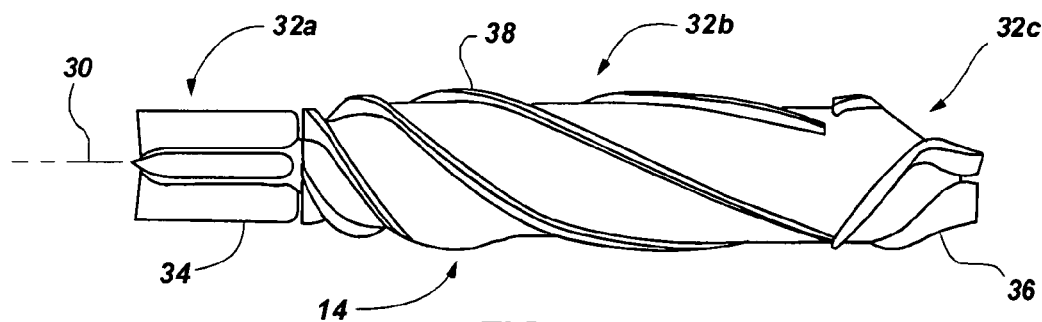
FIG. 5 is a side view of the impeller of FIG. 4, shown with infuser and diffuser blades of the stator and showing inducer, impeller blade and diffuser regions.
Figure 6:
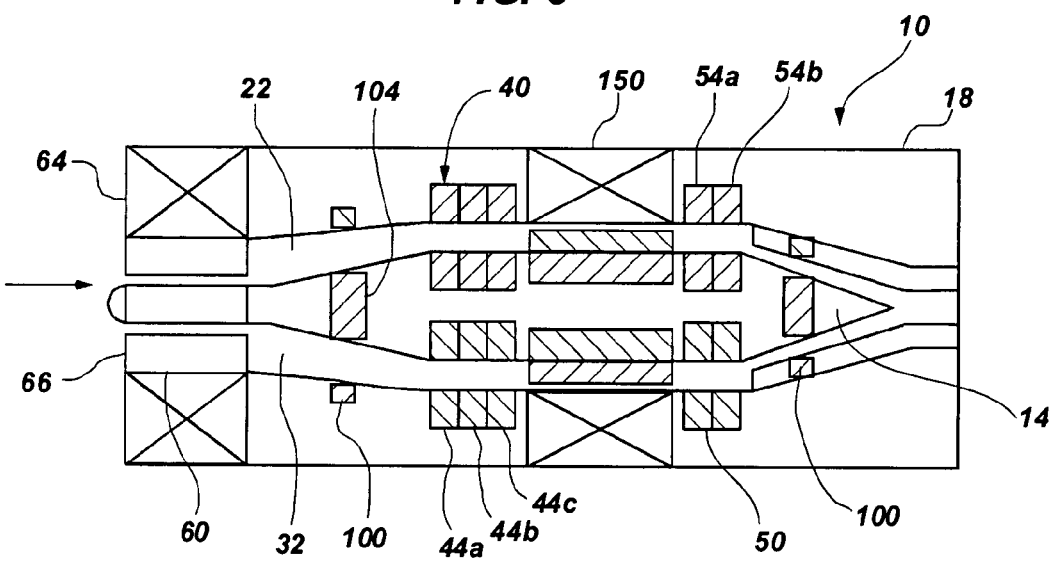
FIG. 6 is a cross-sectional schematic view of the blood pump of FIG. 1 showing a magnetic suspension and rotating system.
Figure 12:
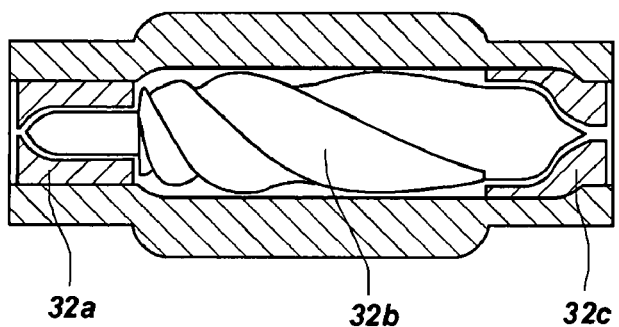
FIG. 12 is a side schematic view of the blood pump of FIG. 1 showing the inducer, impeller blade and diffuser regions.
Figure 13A:
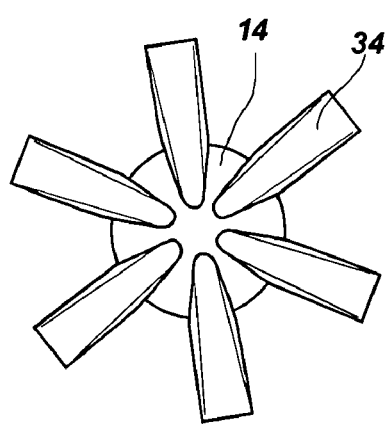
FIGS. 13a and b are an end views of the inducer blades of the blood pump of FIG. 1.
Figure 13B:
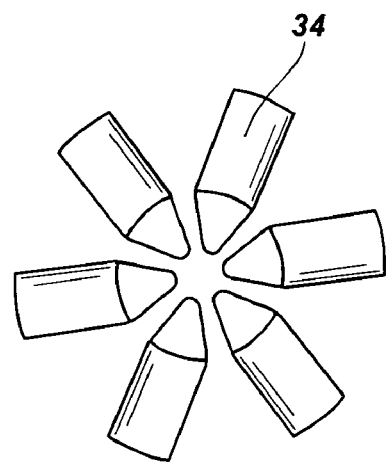

The cavity 22 or pump 10 includes an inducer region 32a, an impeller blade region 32b, and a diffuser region 32c, as shown in FIGS. 5 and 12. The inducer region 32a reduces a tangential flow component or straightens the flow into the pump. The impeller blade region 32b imparts rotational kinetic energy to the fluid. The diffuser region 32c converts the kinetic energy to static pressure.

The inducer region 32a is located near the inlet 26, and includes an infuser with one or more inductor blades 34. The inductor blades 34 are disposed on the stator 18 at the inlet 26 of the cavity 22 and extend in a radial inward direction. In addition, the inductor blades 34 are aligned substantially axially with respect to the axis of rotation 30. Thus, the inductor blades 34 are configured to impose an axial flow (as opposed to a radial or circumferential flow) on the blood as it enters the pump, and resist the impeller from inducing a circular flow upstream of the pump. In one aspect, the inductor can include six blades circumscribing the axis of rotation, as shown in FIGS. 3, 5, 10a, 13a and b. The inductor blades extend into the cavity, but without spanning the cavity. The liner 29 can be formed over and around the inducer blades 34. It is of course understood that more or fewer inducer blades 34 can be provided. In addition, it will be appreciated that the inducer blades can be curved or helical.

Figure 3:
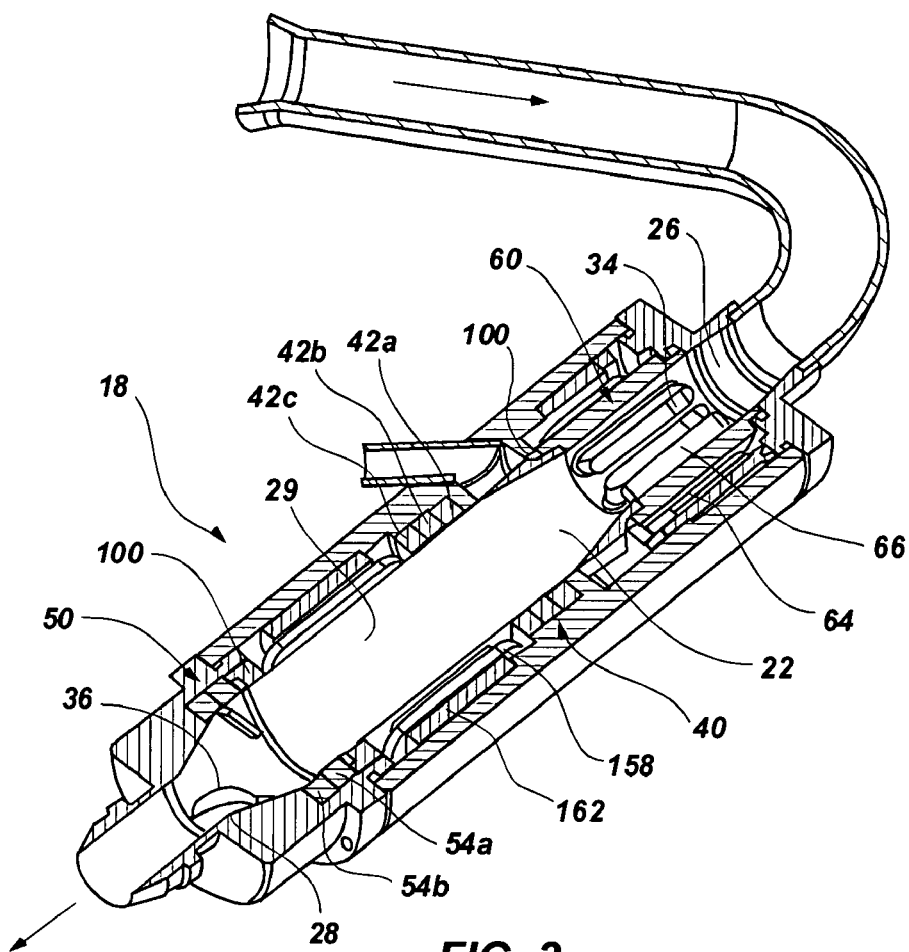
FIG. 3 is a longitudinal cross-sectional perspective view of a stator of the blood pump of FIG. 1.
Figure 4:
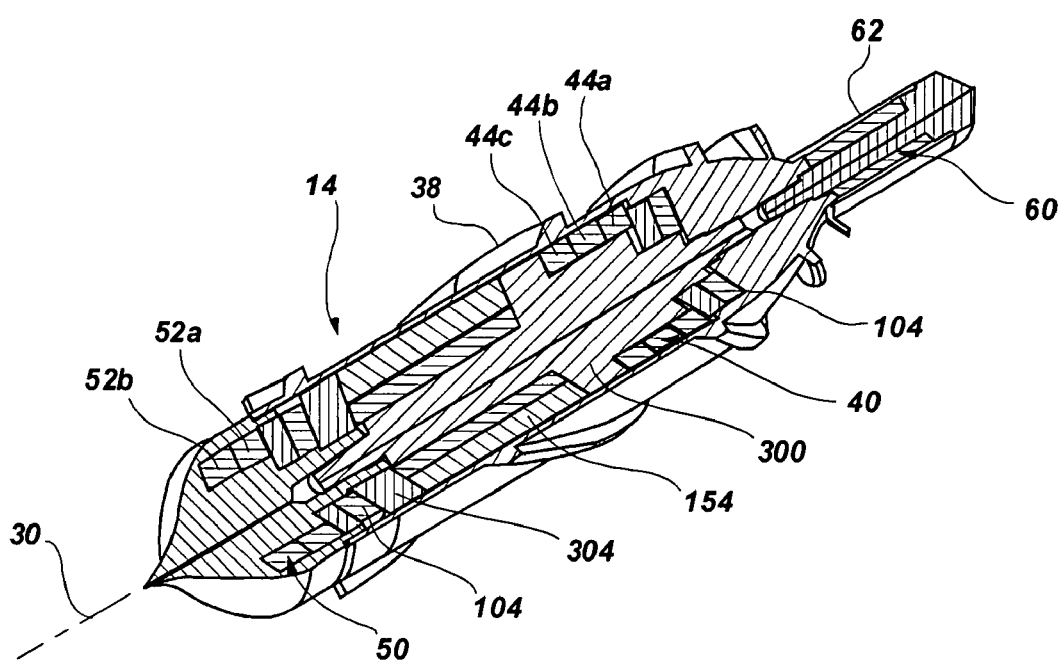
FIG. 4 is a partially broken-away perspective view of an impeller of the blood bump of FIG. 1.
Figure 14A:
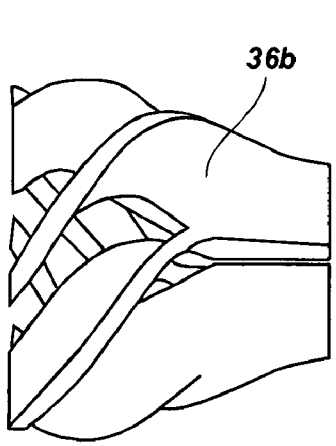
FIGS. 14a and b are side and end views of the diffuser blades of the blood pump of FIG. 1.
Figure 14B:
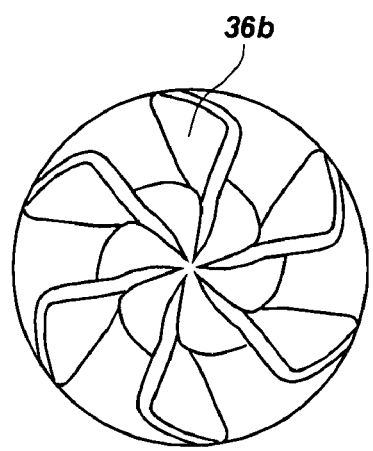

The diffuser region 32c is located near the outlet 28, and includes a diffuser with one or more diffuser blades 36. The diffuser blades 36 are disposed on the stator at near the outlet 28 of the cavity 22 and extend inwardly without spanning the cavity. The diffuser blades 36 are shaped and/or oriented substantially helically with respect to the axis of rotation 30. Thus, the diffuser blades 36 are configured to straighten the flow as it exits the pump. The diffuser can include three diffuser blades 36, as shown in FIGS. 3 and 5, or six diffuser blades 36b, as shown in FIGS. 14a and b. It is of course understood that more or fewer diffuser blades can be provided. The diffuser blades can extend from the liner 29.

The diffuser region converts fluid velocities or kinetic energy into pressure due to the specific shape of the diffuser blades and the diffuser channel. In one aspect, the downstream diameter of the diffuser channel can be slightly larger than the upstream diameter at an inlet to the diffuser channel. The diffuser channel can have a divergence angle being usually less than 5 degrees in order to avoid flow separation. The expansion region in the channel will have a smooth increase in cross-sectional area, thus reducing the axial velocity of the blood flow leaving the pump.

Stationary blades mounted to the diffusion shroud provide a configuration that aids in removing the tangential component of the absolute velocity of the flow. The reduction in velocity further helps to increase the pump's pressure rise and hydraulic efficiency. The curvature of the stationary blades is selected such that the flow enters the diffuser blades with minimum hydraulic loss and leaves the pump axially. The assessment of the diffuser performance is given by the recovery factor, which is a function of the inlet and outlet diffuser flow velocities and the pressure loss within the diffuser due to resistance. The ideal case of a full recovery of the kinetic energy of the flow entering the diffuser is represented by a recovery factor of unity. Maximum values for the recovery factor of 0.7–0.8 indicate an optimum combination between the diameter ratio and length of the channel. The recovery value decreases rapidly for large divergence angles (>10 degrees) due to boundary layer separation.

The current diffuser blade geometry is designed to minimize hydraulic losses at the design point. Therefore, for this operating condition, the leading edge of the diffuser blades perfectly matches the direction of the approaching blood flow velocity vector. At off design operating conditions, there will be a mismatch between fluid approach velocity vectors and the leading edge angle of stationary blades causing additional losses. However, for the operating range of the present invention, these hydraulic losses were maintained at an acceptable level, preserving the diffuser recovery factor.

The impeller blade region 32b is disposed between the inducer and diffuser regions 32a and c. The impeller 14 can have an elongated body with one or more impeller blades or vanes 38 extending radially therefrom. For example, the impeller can have four impeller blades, as shown. It is of course understood that the impeller can be proved with more or fewer impeller blades. The impeller blades 38 can have a helical shape and/or orientation to drive the fluid or blood through the pump as the impeller rotates. The impeller blades 38 and the diffuser blades 36 can have opposite orientations so that the impeller blades 38 impart circular flow in one direction and the diffuser blades 36 straighten the flow.

The magnetic suspension system includes a plurality of magnetic bearings or bearing sets. Each bearing includes one or more impeller magnets associated with the impeller, and one or more corresponding stator magnets associated with the stator. The impeller and stator magnets are disposed across the fluid passage 32 from one another, and substantially radially aligned with respect to the axis of rotation 30. The impeller and stator magnets can be annular or ring magnets with the stator magnet surrounding or circumscribing and concentric with the impeller magnet. The fluid passage 32 can be substantially annular, and can extend between the annular magnets. In addition, the magnetic bearings can include a plurality or series of axially arrayed, abutting magnets on each of the impeller and stator, as described below.

It has been recognized that, under normal operation, the largest force that to be controlled is the axial force due to the relatively large pressure change over the length of the pump. For example, the pressure change across the pump can be as great as 150 mm Hg. The magnetic suspension system includes an axial or thrust bearing 40 to support the impeller axially in the cavity 22. The axial bearing 40 includes a plurality of permanent magnets in an axially aligned, reverse polarity configuration to axially center the pump impeller. The axial bearing 40 can be characterized as an array of adjacent bearing sets arrayed axially with respect to the axis of rotation 30, with an array of impeller magnets 42 and an array of stator magnets 44. For example, three axial bearing sets can be disposed adjacent to, or abutting to, one another. Each bearing set includes an impeller magnet on the impeller and a stator magnet on the stator. The impeller and stator magnets are radially aligned across the fluid passage 32 from one another. Thus, a plurality of adjacent impeller magnets 42a–c is disposed axially on the impeller, and a plurality of adjacent stator magnets 44a–c is disposed axially on the stator. Adjacent impeller magnets, and adjacent stator magnets, have axially aligned polarities, and reverse polarities with respect to adjacent magnets. Thus, the axially aligned polarity of one impeller magnet is reversed with respect to an adjacent impeller magnet. Similarly, the axially aligned polarity of one stator magnet is reversed with respect to an adjacent stator magnet. In addition, the impeller and stator magnets of each bearing set have reversed polarity with respect to one another so that magnets of the axial bearing on opposite sides of the fluid passage have opposite polarity. Thus, the axially polarity of one impeller magnet is reversed with respect to a corresponding stator magnet across the fluid passage.

Figure 7:
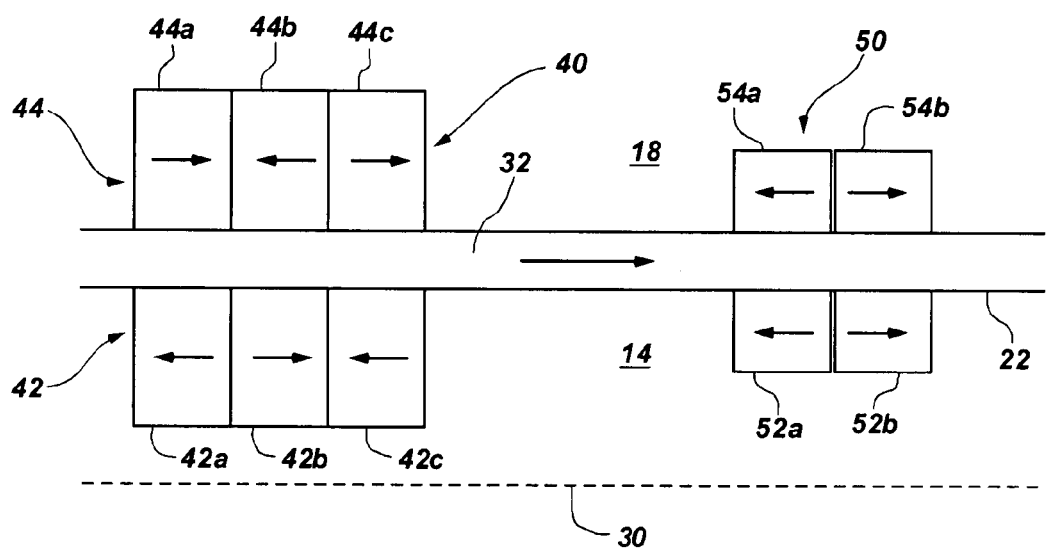
FIG. 7 is a partial, side schematic view of the blood pump of FIG. 1.

The axial bearing 40 can be constructed by several axially polarized individual components or rings. One ring is placed upon the impeller and one on the stator forming a fluid (blood) gap. FIGS. 3, 4, 6 and 7 show the geometry of the magnetic ring pairs that form a thrust bearing. The polarization is different, as shown in FIG. 7, where the polarities are reversed. The North pole on one side of the fluid gap is placed across from the South pole on the other side of the fluid gap. The polarities are reversed at the other end of the rings. This configuration produces a positive axial stiffness and a negative radial stiffness.

A single pair of permanent magnets rings may not produce enough axial stiffness. The axial stiffness is strongly enhanced by constructing a thrust bearing composed of several rings of reversed polarity, as shown in FIG. 7 for three rings. This combination of rings strongly increases the axial stiffness of the axial bearing. A different number of rings can be used. The rings may or may not be of the same axial length.

The stator mounted permanent magnet configuration and the impeller mounted permanent magnet configuration have a straight through clearance gap so that they can accommodate the once through axial blood path without any axial obstruction. The axial permanent magnet uses no power to axial center the rotor, so it assists with the reduction of power consumption. The configuration in this pump that produces this straight through flow path is the axially polarized permanent magnet alternating pole configuration with magnets aligned axially on both the stator and rotor without a large thrust disk.

The magnetic suspension system also includes a radial permanent magnet bearing 50 to support the impeller radially in the cavity 22. The axial bearing 40 can be characterized as at least a pair of adjacent bearing sets positioned axially with respect to the axis of rotation 30. For example, two axial bearing sets can be disposed adjacent to, or abutting to, one another. Each bearing set includes an impeller magnet on the impeller and a stator magnet on the stator. The impeller and stator magnets are radially aligned across the fluid passage 32 from one another. Thus, a plurality of adjacent impeller magnets 52a and b is disposed axially on the impeller, and a plurality of adjacent stator magnets 54a and b is disposed axially on the stator. Adjacent impeller magnets, and adjacent stator magnets, have axially aligned polarities, and reverse polarities with respect to adjacent magnets, similar to that described above with respect to the axial bearing. In addition, the impeller and stator magnets of each bearing set have the same polarity with respect to one another so that magnets of the radial bearing on opposite sides of the fluid passage have the same polarity, opposite that described above with respect to the axial bearing.

The radial bearing 50 can be constructed of axially polarized permanent magnet rings. The rings can be of the same length. Alternatively, the rings can have different lengths. One set of ring is placed upon the impeller, and one set of rings on the stator forming a fluid (blood) gap. (The axial polarities are the same as indicated by the arrows with the North pole at the head of the arrow and the South pole at the tail of the arrow.) The rotor and stator North poles are placed on opposite sides of the fluid gap while the rotor and stator South poles are placed on opposite sides of the fluid gap. This creates a positive stiffness so that the rotor and stator have equal and opposite forces acting to keep them from moving closer together. However, this configuration also produces a negative axial stiffness, of twice the positive radial stiffness, that must be compensated for by other bearing components.

A single pair of magnetic rings may not provide enough stiffness to keep the impeller centered. A higher stiffness radial bearing can be constructed by combining several rings with similar polarity next to one another. This configuration strongly enhances the stiffness values beyond the number which is obtained by multiplying the stiffness of one ring by the number of rings. A different number of rings can be used. The rings may or may not be of the same axial length.

Thus, the axial and radial bearings 40 and 50 utilize a new permanent magnetic pole configuration with compact, high magnetic strength magnet rings with axially polarized alternating polarity. This configuration enables axial suspension of the impeller and radial suspension of the impeller at one end without any external power. Also, the permanent magnet bearings do not require any feedback control or position sensors to operate. These bearing configurations can be placed in the impeller and stator in a manner which does not intrude into the blood flow path enabling a straight through blood flow path for the rotary blood pump.

Figure 8:
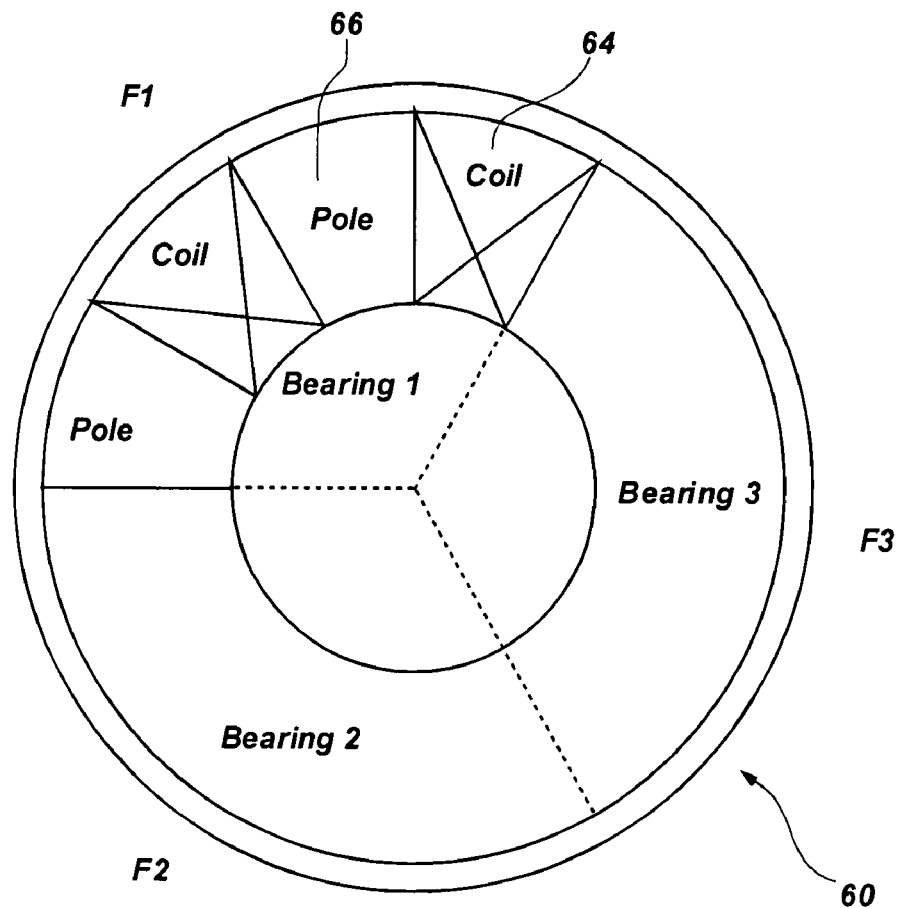
FIG. 8 is a schematic end view of the blood pump of FIG. 1 showing an active, electromagnetic bearing.

The magnetic suspension system also includes a radial electromagnetic bearing 60 to support the impeller radially in the cavity 22. The radial electromagnetic bearing 60 can be a six pole, actively controlled, electromagnet with impeller magnets 62 disposed in the impeller 14, and coils/poles (coils 64 and poles 66) associated with the stator 18. The impeller magnets 62 and coils/poles are positioned radially across the fluid passage 32 from one another. The stator can include a series of radial stator poles 66 constructed of a non-permanent magnetic material, such as silicon iron, which are activated and powered by the coils 64 wrapped around the legs as shown in FIG. 8 and similar materials forming a cylindrical configuration on the impeller. In one aspect, the wiring is configured in such a way that the currents generate magnetic flux producing a North pole in one of the electromagnet poles of a pair, and the other produces a South pole in the other one of the pair. In the configuration shown, the six pole electromagnet shown in FIG. 8, there are three pairs of poles. A smaller number or greater number of electromagnetic poles may be employed to reduce or increase the size of the bearing as needed with an associated reduction or increase in the force capability of the bearing.

Figure 9:
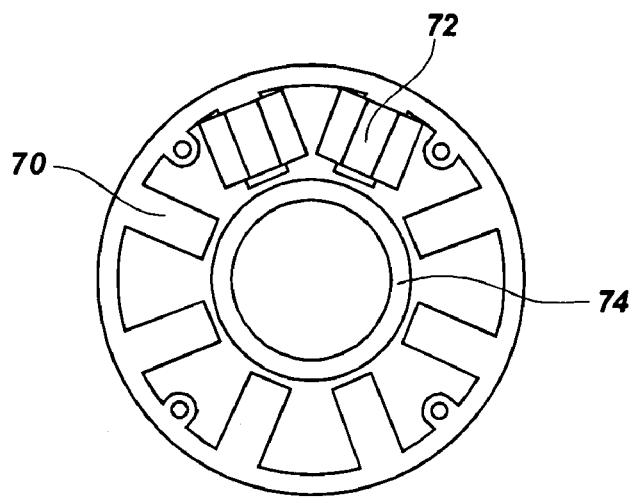
FIG. 9 is a partial end view of a prior art active bearing.

In one aspect, the active electromagnetic bearing 60 can include: position sensors, magnetic actuators, and a source that supplies and drives the currents through each of the magnetic actuators. Referring to FIG. 9, an example of a typical, prior art radial active magnetic bearing construction is shown with a radial stator 70 with coils 72 that from the actuators, and a rotor 74 whose radial position is governed by the amount of flux, or composite force, that is generated within each of the actuators. The stator generally is a single monolithic piece of "soft" magnetic material, such as silicon iron (SiFe), which provides a low reluctance pathway for the magnetic fields generated by the actuators. Generally, this radial stator assembly also provides a means for securing this structure to the housing, such as four through holes (one in each quadrant) that provide for axial attachment of the stator to the housing. The prior art assembly method for a radial active magnet bearing include "slipping" each of the radial coils 72 onto each "leg" of the stator 70, and then inserting and securing the stator into its respective housing. The purpose of the prior art active magnetic bearing is to provide the force, via the flux generated within the structure, to position and hold the rotor 74 in its centered position.

Figure 10A:
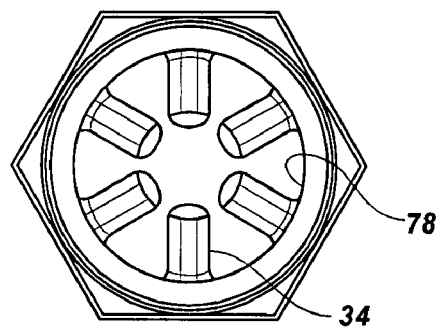
FIG. 10a is a partial end view of the blood pump of FIG. 1 showing a combination of inducer blades and active, electromagnetic bearing poles.

In one aspect, the pump of the present invention can combine the infuser or inductor blades 34 with the active electromagnetic bearing 60. The poles 66 of the active bearing can extend into, or can be combined with, the inductor blades 34. Referring to FIGS. 10a and b, the inducer region of the stator 18 and a portion of the active electromagnetic bearing 60 is shown with the active electromagnetic bearing 60 and infuser blades 34 incorporated together. The electromagnetic bearing poles 66 can be placed in the pump inducer where the poles are covered by solid material in the shape of a fluid blade to strengthen and enhance the pump inlet flow. Thus, the bearing poles 66 can be disposed in the infuser blades 34. This dual use of the pole/blade configuration provides a compact multi-use design for these pump components. This dual use also makes efficient use of the space and volume allotted. Thus, the active magnetic stator and inducer are combined, as are their two functions, into one composite dual use device.

Figure 10E:
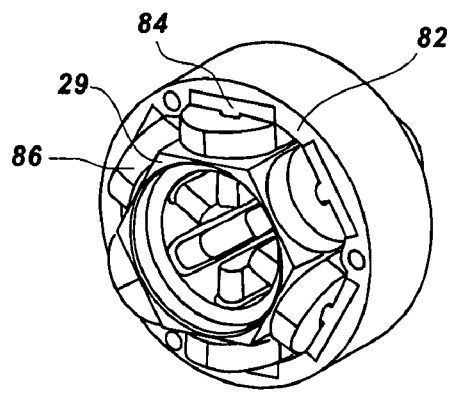
FIGS. 10c–e are partial perspective views of the blood pump of FIG. 1 showing one method for assembling the active, electromagnetic bearing poles with the inducer blades.
Figure 10B:
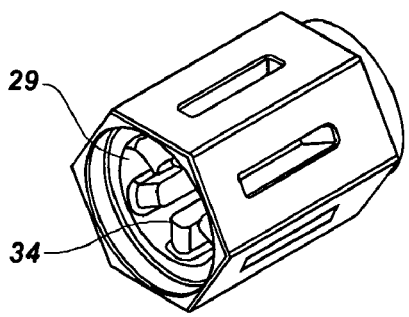
FIG. 10b is a partial perspective view of the blood pump of FIG. 1 showing the combination of inducer blades and active, electromagnetic bearing poles.

The inducer can include a non-magnetic material, such as titanium, that provides a unimpeded magnetic pathway for the flux generated within the stator, while it also provides a means for sealing the fluid (blood) that passes through the interior of the inducer from being cross contaminated by the stator magnetic components. This form of protective enclosure is referred to as a liner or "can" 29. It would be difficult to insert a rigid monolithic active magnetic bearing stator structure within the monolithic form of the inducer. Thus, a combined inducer and active magnetic bearing stator is assembled, as shown in FIGS. 10c–10e. Referring to FIG. 10c, an active magnetic bearing leg and coil subassembly 80 is shown with a stator backiron 82. An individual stator leg 84 with a "T"-shape or cross-section includes opposite "dovetail" surfaces on either end of the horizontal portion of the leg. These dovetail surfaces mate with an inverted or mating dovetail slot 85 in the stator backiron 82. A coil 86 fits around the perimeter of the vertical portion of the "T"-shape and is shown coincident to the bottom of the horizontal portion of the "T". Referring to FIG. 10d, six subassemblies 80 are shown inserted into pockets 88 provided in the inducer or can 29. Referring to FIG. 10e, the dovetails of the subassemblies 80 are axial inserted within the dovetail slots 85 of the backiron 82.

Figure 10F:
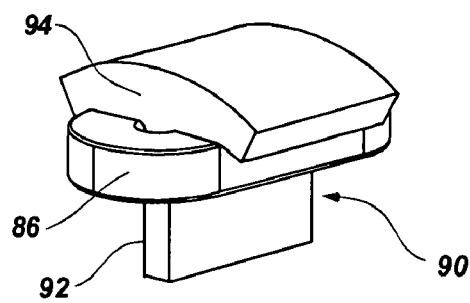
FIGS. 10f–h are partial perspective and end views of the blood pump of FIG. 1 showing another method for assembling the active, electromagnetic bearing poles with the inducer blades.
Figure 10C:
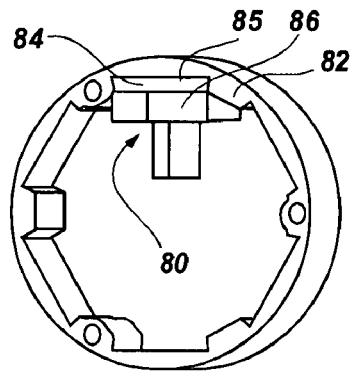
Figure 10G:
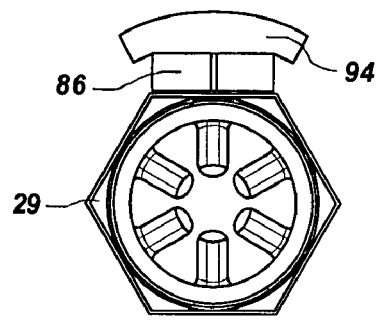
Figure 10D:
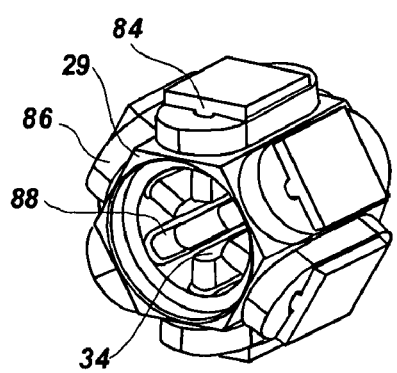
Figure 10H:
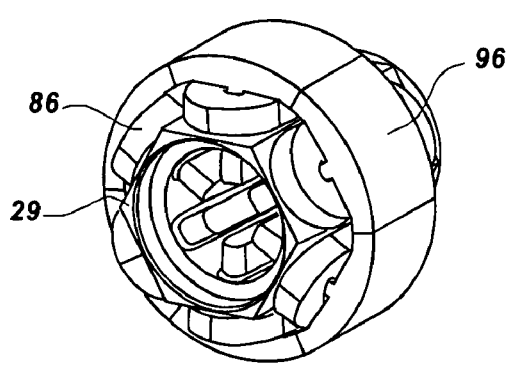

Referring to FIGS. 10f-h another method of assembling a combined active magnetic bearing and inducer is shown. An integral or monolithic leg and backiron 90 includes a leg portion 92 and a 60 degree arc portion 94 of the completed backiron 96. A coil 86 fits around a perimeter of the leg portion. A 60 degree arc has been used by way of example, because the inducer can include six blades. A different number of legs or blades may be used, as well as unequal arc segments. Again, the leg portion 92 is inserted into pockets of the can 29.

As shown, the plurality of magnetic bearings can be positioned with the radial electromagnet bearing 60 disposed nearer the inlet 26 to the fluid passage; the radial permanent magnet bearing 50 disposed nearer the outlet 28 to the fluid passage; and the axial permanent magnet bearing 40 disposed intermediate the radial electromagnet bearing and the radial permanent magnet bearing.

In addition, the pump 10 includes a motor 150 with impeller magnets 154 on the impeller 14 and coils/poles (coils 158 and poles 162) associated with the stator 18. For example, the motor can be a brashness DC motor with no brushes to wear out and a compact, power efficient construction. In addition, the motor can have an offset stator pole structure such that it can only be started up in one direction—the proper or desired direction for the impeller to pump.

Furthermore, the motor can be a unidirectional motor. The motor can include a brashness DC motor configuration which can only start-up in the needed direction of movement consistent with the impeller flow design and a self-tuning controller. The motor can include off-set stator poles which taper to create a magnetic gap between a leading pole edge in a desired direction of rotation smaller than another magnetic gap between a trailing pole edge in an opposite direction of rotation. The motor can be a six pole configuration with tapered poles, three phase stator winding and a four segment permanent magnet target in the rotor. Thus, there are no brushes to wear out and the motor has a compact, power efficient construction. In addition, the motor has a special offset stator pole structure, such that it can only be started up in one direction—the proper direction for the impeller to pump. The proper startup torque direction is produced with a tapered pole design. The motor pole construction has a taper such that the magnetic gap clearance of the leading motor pole edge, in the direction of rotation, is made smaller than the magnetic gap clearance of the motor pole trailing edge, in the opposite direction of rotation. The motor can also include a self tuning controller with a microprocessor controller inverter. Unlike previous rotary blood pumps that call for an angular position sensor, the present motor and controller do not require any sensor to determine commutation or rotational speed. The self tuning controller utilizes auto-parameter tuning upon start up, in torque overload situations, high temperature protection, and active rotational speed control. This inverter provides high efficiency while reducing any radio frequency noise generation.

The magnetic suspension system described above, along with the rotating system or motor, provides a marked improvement over previous magnetic suspension systems requiring both primary and secondary blood paths. The present magnetic suspension system enables an unobstructed, one-pass blood design, without a secondary blood path for the magnetic suspension clearances. Thus, secondary flow paths are avoided which minimize the incidence of flow stasis leading to thrombosis as well as hemolysis.

The single, unobstructed blood path, and the fluid passage, is defined by an annular gap positioned radially between all of the magnetic bearings and the motor. Thus, all of the magnetic bearings have stator magnets disposed radially across the fluid passage from corresponding impeller magnets. Similarly, the motor has coils/poles disposed radially across the fluid passage from corresponding impeller magnets. Thus, the annular gap is positioned radially between the impeller and the stator, and positioned radially between all of the plurality of magnetic bearings. The fluid passage or single, unobstructed blood path extends through the stator and around the impeller, between the permanent magnet and electromagnetic bearings. Thus, the impeller is magnetically suspended within the cavity of the stator without structure spanning the cavity of the stator.

The pump can be controlled and powered by a controller box, that may be implanted or external to the body, and that can provide coil currents to the motor and active bearing. The controller box can include control electronics or computers, and a power supply. The power supply can include a long term battery carried on the body, and a small internal battery in the controller box for short term back up use. If the control box is implanted, the long term battery power can be supplied either by a transcutaneous wire or a high frequency transfer (telemetry) through the intact skin. If the control box is carried externally, long term battery power can be supplied by wire.

Power amplifiers can be employed to operate the electromagnetic bearing coils based upon input signals from coil control signal processing boards. The coil controller boards can be programmed with an automatic feedback control algorithm to keep the pump impeller positioned at or near the center of the fluid gap clearance when subject to various fluid, gravitational or other disturbance forces. The automatic feedback control algorithm can utilize the rotor radial coordinate position, in two coordinate directions, relative to the stator or pump housing and impeller axial coordinate position relative to the pump housing as the feedback signal. These impeller position signals can be provided by sensors, such as Hall sensors or eddy current sensors. The feedback signal may include other inputs, such as pump accelerations in one, two, or three directions as measured by an accelerometer.

The radial and axial positions can be detected by Hall sensors which include very compact, low power electronic operated, sensitive sensors of magnetic fields. Several of these sensors can be placed in the pump housing in multiple radial positions, and at least two axial positions. At least some of the Hall effect sensors 200 can be placed where the fluid gap tapers so that the magnetic field varies with both radial and axial position changes so that both are evaluated from a simple algorithm and thus the position changes are measured in both directions. The Hall effect sensors can be powered by the same long term (or short term) battery system as the electromagnetic bearing.

Permanent magnets 204 can be placed in the impeller in positions adjacent to the locations of the Hall effect sensors in the stator or pump housing. The permanent magnets 204 provide the changes in magnetic field signal, as the rotor moves radially or axially, for the Hall effect sensor to evaluate. These Hall effect sensors detect the displacement of the impeller relative to the sensor in both radial and axial directions, and provide part or all of the feedback control signal used for the electromagnetic bearing, as well as the physiological controller. Also, they provide signals which will be monitored by the controller unit to provide alarms, or other suitable methods to make the patient or medical personnel aware of existing or potential problems, such as impeller rubbing. Signals may be used for monitoring by the pump control unit, or telemetered to an external monitoring/alarm unit.

Using the Hall effect sensors eliminates the problems of space constraints requirements for the sensors, the energy budget required for the sensors, placing sensor faces within the stator housing, contamination of the blood stream, and thrombosis and clots. The Hall effect sensors use the Hall "effect" to measure the field surrounding a magnetic device. Linear versions of these devices are able to accurately plot the magnetic field intensity surrounding a magnetic device. Four Hall effect sensors can be arranged in an orthogonal array, two on both the X and Y axes, then by differentiating the axis pairs, the position of the magnet within these devices can be obtained. One advantage of using a Hall effect sensor in this miniature blood pump is that the flux lines emanating from the magnet will easily pass through the fluid (blood) without contamination, and the magnet and Hall effect sensor can both be sealed behind in a non-magnetic barrier that is referred to as a liner or "can".

Figure 11A:
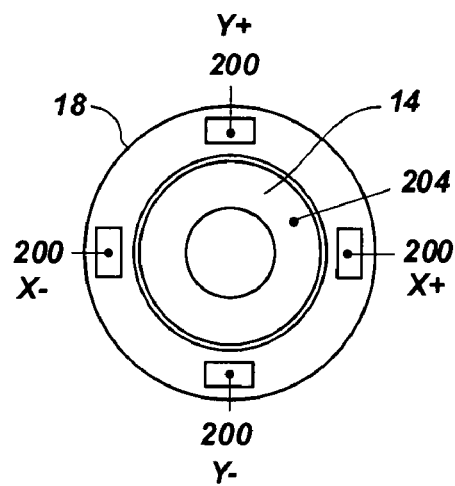
FIGS. 11a and b are schematic end and side views of a sensor array of the blood pump of FIG. 1.
Figure 11B:
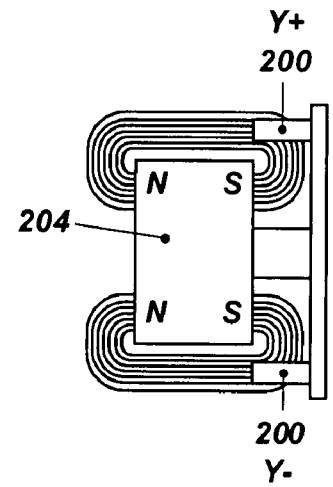
FIG. 11c is a schematic side view of another sensor array of the blood pump of FIG. 1.

Referring to FIGS. 11a and b, one embodiment of a Hall effect sensor array is shown. As show in FIG. 11a, four Hall effect sensors (X+, X−, Y+, and Y−) are shown attached and mounted orthogonally to a printed circuit board (PCB) as a Hall sensor array, and a cylindrical magnet 74 is centered in between these Hall effect sensors. Referring to FIG. 11b, stylized magnetic flux lines are shown emanating from the magnet 70 that represent only one plane (Y) of flux line distribution about the magnet, where these flux lines are shown intercepting the Y+ and Y− Hall effect sensor. It will be appreciated that if the magnet is centered in between the Y+ and Y− Hall effect sensor, these two devices will output a voltage of equal amplitude. It will also be realized, that if the output from these two devices are assigned the +Y and −Y respective relationships, and these values are then differentiated, the signed differentiated output will be an indication of the magnet position above or below the abscissa, and the value of this output will be the amount of positional offset from the abscissa. Likewise, the X position of the magnet within the sensor array can be obtained by following this same procedure. The mathematical relationship for the X and Y positions would be 3X=X−X+, and 3Y=Y−Y+. It will also be appreciated that the magnetic flux lines from the magnet are impervious to any non-ferrous material, so that a biocompatible "can" or protective barrier that is made of titanium, for example, would not impede or hinder the positional information obtained from this device.

Figure 11C:
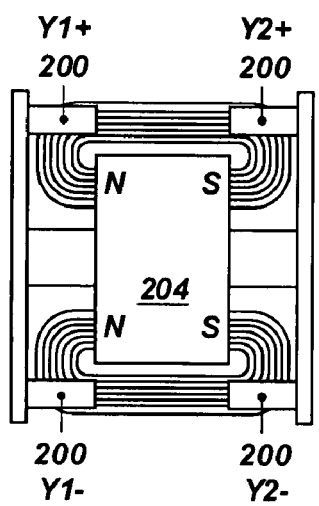

Referring to FIG. 11c, another embodiment of a Hall effect array configuration is shown with two Hall effect arrays placed axially symmetric about the centerline and mid plane of a magnet. It will be appreciated that the X1, Y1, X2 and Y2 differentiated pairs will work as independent sensors for determining the relative X and Y magnet position at their respective locations. It will also be appreciated that in addition to the X and Y positions, the relative axial location of the magnet can be derived by separately summing the all of X1 and Y1 Hall effect outputs without regards to the sign (31=(X1+)+(X1−)+(Y1+)+(Y1−)), while simultaneously doing the same with X2 and Y2 outputs (32). Assigning an arbitrary sign of + of axial motion towards the right (X2 and Y2) arrays, and—as motion towards the left (X1 and Y1) arrays, and adding these two summations together will yield the direction of axial offset as well as the Z value of the magnet position. The mathematical relationship for determining the Z position of the magnet, assuming motion towards the right would be positive, would be Z=32−31.

The above described Hall effect sensors or arrays do not require an unobstructed vision of the impeller. Thus, the sensors can be separated from the impeller and fluid passage by the lining or can. In addition, the sensors do not intrude into the fluid passage, and thus do not impede the flow path or fluid characteristics. In addition, the sensors do not require any special surfaces to locate the position of a rotating member. For example, laser sensors require highly polished surfaces, and Eddy Current (inductive) and capacitive sensors require a conductive (metallic) surface. In addition, the sensors do not require an additional magnet to be added to the rotating member. For example, two permanent magnet arrays can be placed within the impeller body, as shown. Therefore, the two Hall effect sensor arrays that are described above could be judicially placed within the stator to view the radial permanent magnets on the impeller and the axial permanent magnets on the impeller. Furthermore, the sensors can be used in conjunction with the motor characteristics (RPM and consumed power) to determine the pressure differential across the pump. This feature could be very important in inferring the high and low blood pressure in a patient.

Alternatively, the Hall effect sensors can be positioned to utilize the impeller magnets of the axial and radial bearings, as opposed to the additional magnets. Thus, two Hall effect sensor arrays can be positioned on the stator, with one being positioned to sense a magnetic field produced by the impeller magnets of the axial permanent magnet bearing, and another positioned at a different axial location to sense a different magnetic field produced by the impeller magnets of the radial permanent magnet bearing.

One or more accelerometers can be used to measure accelerations of the stator or pump housing in different directions. Also, velocity measurement devices may be employed to determine the velocity of the pump housing in different directions. The signals from these devices may be employed to serve as feedback signals for the electromagnet, as well as the physiological controller and/or alarms such as to indicate a fall.

In addition, the active electromagnetic bearing itself can be viewed both as an actuator and a sensor. Thus, the active bearing can be used in a self-sensing mode to extract the position information from the coil. An estimator can be built to filter the current signal and obtain the position from the filtered signal. Such a technique eliminates additional sensors and electronics. Therefore, the number of wire leads is reduced, so does the reliability.

Referring again to FIG. 4, the impeller can include a tie bolt 300 and expendable material 304 that can be used to balance the rotor.

The impeller and diffuser can be manufactured by a titanium casting using a lost wax method in which a precise wax model or positive is formed in a ceramic shell and negative. Liquid titanium can be poured into the ceramic shell, and the shell cracked open after cooling. Hydrogen pressure implantation can be applied to the cast object to remove any surface imperfections, followed by a chemical etch to prepare the surfaces for machining and polishing. The blood flow path can be polished to a 10 micro-inch surface finish or better. The inlet cannula and the inducer can be produced with standard metal forming techniques. The inlet cannula can be titanium tubing that is formed (bent and flared) into the desired shape. The inner surface can be polished to 10 micro-inch surface finish. The inducer can be manufactured using a combination of CNC milling, wire electrical discharge machining (EDM) and plunge EDM techniques. Alternatively, the inducer could be cast as discussed above. Polishing can be accomplished using the extrude hone method, which involves using a fine cutting medium, such as diamond chips, suspended within a slurry-like medium to polish and remove any surface imperfections. The slurry can be pumped or passed along the surfaces to be polished until desired surface finish is achieved.

In accordance with one aspect of the invention, the pump can be configured to pump fluids or liquids other than blood.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. A blood pump, comprising:
   a stator having a cavity extending therethrough;
   an impeller, rotatably disposed and magnetically suspended within the cavity of the stator, the impeller defining an axis of rotation, and the stator and impeller defining a fluid passage therebetween;

a plurality of magnetic bearings, including passive permanent magnet and active electromagnetic bearings, suspending the impeller within the cavity of the stator, and having impeller magnets on the impeller and stator magnets or coils/poles on the stator;

a motor including impeller magnets on the impeller and coils/poles associated with the stator;

a single, annular blood flow path extending axially through the cavity between a cylindrical wall of the cavity of the stator and the impeller at least around blades of the impeller, with the cylindrical wall of the cavity of the stator forming a continuous outer cylindrical surface of the annular blood flow path having a circular cross section, the continuous outer cylindrical surface reducing boundary layer separation, recirculation, stagnation and wake in blood flowing through the annular blood flow path; and an inducer region with at least one inducer blade extending radially inward from the stator near the inlet without spanning the cavity; and a diffuser region with at least one diffuser blade extending inward from the stator near the outlet without spanning the cavity.

2. A blood pump in accordance with claim 1, wherein all the impeller magnets and corresponding stator magnets or coils/poles of the magnetic bearings and motor are disposed radially across the single, annular blood flow path.

3. A blood pump in accordance with claim 1, wherein the cavity of the stator has a substantially cylindrical shape tapering at the inlet and the outlet; and wherein the impeller has a substantially cylindrical shape tapering at opposite ends.

4. A blood pump in accordance with claim 1, wherein the single, annular blood flow path extends axially through the cavity without any secondary flow paths or recirculating flow paths.

5. A blood pump in accordance with claim 1, wherein all of the magnetic bearings and the motor share a common longitudinal axis.

6. A blood pump in accordance with claim 1, wherein the impeller is magnetically suspended within the cavity of the stator without structure spanning the cavity of the stator.

7. A blood pump in accordance with claim 1, wherein all of the passive permanent magnetic bearings include passive permanent impeller magnets disposed in the impeller, and passive permanent stator magnets disposed on the stator and around the cavity of the stator, without any passive permanent stator magnet disposed in the cavity of the stator.

8. A blood pump in accordance with claim 1, further comprising:

a can, radially surrounding the cavity of the stator, and separating the coils/poles of the stator from the fluid passage.

9. A blood pump in accordance with claim 1, wherein the plurality of magnetic bearings further comprises:

a) a radial, active, electromagnet bearing, disposed nearer an inlet to the fluid passage, to radially support the impeller in the cavity, including:
   i) an impeller magnet, disposed nearer a leading end on the impeller; and
   ii) a plurality of poles and coils, disposed on the stator radially across the fluid passage from the impeller magnet;

b) an axial, passive, permanent magnet bearing, disposed intermediate along the fluid passage, to axially support the impeller in the cavity, including:
   i) a plurality of impeller magnets, disposed intermediate along the impeller, the impeller magnets having axially oriented polarities with sequentially altering polarity; and
   ii) a plurality of stator magnets, disposed on the stator radially across the fluid passage from the impeller magnets, the stator magnets having axially oriented polarity with sequentially alternating polarity; and
   iii) the impeller and stator magnets being radially aligned across the fluid passage from one another with the polarity of the impeller and stator magnets oppositely aligned with opposite polarities radially aligned across the fluid passage; and c) a radial, passive, permanent magnet bearing, disposed nearer an outlet of the fluid passage, to radially support the impeller in the cavity, including:
   i) a plurality of impeller magnets, disposed near a trailing end of the impeller, the impeller magnets having axially oriented polarities with sequentially alternating polarity; and
   ii) a plurality of stator magnets, disposed on the stator radially across the fluid passage from the impeller magnets, the stator magnets having axially oriented polarities with sequentially alternating polarity; and
   iii) the impeller and stator magnets being radially aligned across the fluid passage from one another with the polarities of the impeller and stator magnets commonly aligned with common polarities radially aligned across the fluid passage.

10. A blood pump in accordance with claim 9, wherein the impeller and stator magnets of the axial, passive, permanent magnet bearing have reversed polarity with respect to one another.

11. A blood pump in accordance with claim 9, wherein the impeller and stator magnets of the radial, passive, permanent magnet bearing have the same polarity with respect to one another.

12. A blood pump in accordance with claim 9, further comprising:

at least two Hall effect sensors, associated with the stator, one of the Hall effect sensors being positioned to sense a magnetic field produced by the impeller magnets of the axial, passive, permanent magnet bearing, and another Hall effect sensor positioned at a different axial location to sense a different magnetic field produced by the impeller magnets of the radial, passive, permanent magnet bearing.

13. A blood pump in accordance with claim 9, wherein the plurality of magnetic bearings further includes an axial bearing to support the impeller axially in the cavity, including:

an array of adjacent bearing sets arrayed axially with respect to the axis of rotation, each bearing set including an impeller magnet on the impeller and a stator magnet on the stator, the impeller and stator magnets being radially aligned across the fluid passage from one another; and adjacent impeller magnets and adjacent stator magnets having axially aligned polarities and reverse polarities with respect to adjacent magnets.

14. A blood pump in accordance with claim 13, wherein the impeller and stator magnets of each bearing set have reversed polarity with respect to one another.

15. A blood pump in accordance with claim 9, wherein the plurality of magnetic bearings further includes a radial permanent magnet bearing, including:

at least a pair of adjacent bearing sets positioned axially with respect to the axis of rotation, each bearing set including an impeller magnet on the impeller and a stator magnet on the stator, the impeller and stator magnets being radially aligned across the fluid passage from one another;

adjacent impeller magnets and adjacent stator magnets having axially aligned polarities and reverse polarities with respect to one another.

16. A blood pump in accordance with claim 15, wherein the impeller and stator magnets of each bearing set of the radial permanent magnet bearing have the same polarity with respect to one another.

17. A blood pump in accordance with claim 9, wherein the plurality of magnetic bearings further includes a radial electromagnetic bearing, including:

impeller magnets, disposed in the impeller; and
coils/poles, associated with the stator;
the impeller magnets and the coils/poles positioned radially across the fluid passage from one another.

18. A blood pump in accordance with claim 17, further comprising:

inductor blades, disposed on the stator at an inlet of the cavity;
the poles of the radial electromagnet bearing being disposed within the inductor blades.

19. A blood pump in accordance with claim 1, wherein the impeller has an elongated straight portion on a leading end.

20. A blood pump, comprising:
a) a stator having a cavity extending therethrough;
b) an impeller, rotatably disposed and magnetically suspended within the cavity of the stator, the impeller defining an axis of rotation, and the stator and impeller defining a fluid passage therebetween;
c) a radial, active, electromagnet bearing, disposed nearer an inlet to the fluid passage, to radially support the impeller in the cavity, including:
   i) an impeller magnet, disposed nearer a leading end on the impeller; and
   ii) a plurality of poles and coils, disposed on the stator radially across the fluid passage from the impeller magnet;
d) an axial, passive, permanent magnet bearing, disposed intermediate along the fluid passage, to axially support the impeller in the cavity, including:
   i) a plurality of impeller magnets, disposed intermediate along the impeller, the impeller magnets having axially oriented polls with sequentially altering polarity; and
   ii) a plurality of stator magnets, disposed on the stator radially across the fluid passage from the impeller magnets, the stator magnets having axially oriented polls with sequentially alternating polarity; and
   iii) the impeller and stator magnets being radially aligned across the fluid passage from one another with the polls of the impeller and stator magnets oppositely aligned with opposite polls radially aligned across the fluid passage;
e) a radial, passive, permanent magnet bearing, disposed nearer an outlet of the fluid passage, to radially support the impeller in the cavity, including:
   i) a plurality of impeller magnets, disposed near a trailing end of the impeller, the impeller magnets having axially oriented polls with sequentially alternating polarity; and
   ii) a plurality of stator magnets, disposed on the stator radially across the fluid passage from the impeller magnets, the stator magnets having axially oriented polls with sequentially alternating polarity; and
   iii) the impeller and stator magnets being radially aligned across the fluid passage from one another with the polls of the impeller and stator magnets commonly aligned with common polls radially aligned across the fluid passage;
f) a motor including impeller magnets on the impeller and coils/poles associated with the stator; and
g) a single, annular blood flow path extending axially through the cavity between the impeller and the stator, and between the impeller magnets on the impeller and the stator magnets or the coils/poles on the stator.

21. A blood pump, comprising:

a stator having a cavity extending therethrough;

an impeller, rotatably disposed and magnetically suspended within the cavity of the stator, the impeller defining an axis of rotation, and the stator and impeller defining a fluid passage therebetween;

a plurality of magnetic bearings, including passive permanent magnet and active electromagnetic bearings, suspending the impeller within the cavity of the stator, and having impeller magnets on the impeller and stator magnets or coils/poles on the stator, and further including:

an axial bearing to support the impeller axially in the cavity, including:

an array of adjacent bearing sets arrayed axially with respect to the axis of rotation, each bearing set including an impeller magnet on the impeller and a stator magnet on the stator, the impeller and stator magnets being radially aligned across the fluid passage from one another;

adjacent impeller magnets and adjacent stator magnets having axially aligned polarities and reverse polarities with respect to adjacent magnets;

a motor including impeller magnets on the impeller and coils/poles associated with the stator; and a single, annular blood flow path extending axially through the cavity between a cylindrical wall of the cavity of the stator and the impeller at least around blades of the impeller, with a cylindrical wall of the cavity of the stator forming a continuous outer cylindrical surface of the annular blood flow path having a circular cross section, the continuous outer cylindrical surface reducing boundary layer separation, recirculation, stagnation and wake in blood flowing through the annular blood flow path.

* * * * *

UNITED STATES PATENT AND TRADEMARK OFFICE
CERTIFICATE OF CORRECTION

PATENT NO. : 7,229,258 B2 Page 1 of 1
APPLICATION NO. : 10/950176
DATED : June 12, 2007
INVENTOR(S) : Wood et al.

It is certified that error appears in the above-identified patent and that said Letters Patent is hereby corrected as shown below:

CORRECT PATENT:
Column 1; lines 13-19 from:

GOVERNMENT RIGHTS

The U.S. Government has a paid-up license in this invention and the right in limited circumstances to require that the patent owner to license others on reasonable terms as provided for by the terms of Grant No. NIH HL64378 awarded by the National Institutes of Health (NIH).

TO:

GOVERNMENT LICENSE RIGHTS

This invention was made with government support under Grant No. NIH HL-64378 awarded by National Institutes of Health (NIH). The government has certain rights in the invention.

Signed and Sealed this

Twenty-first Day of August, 2007

JON W. DUDAS
*Director of the United States Patent and Trademark Office*